(12) United States Patent
Weh

(10) Patent No.: US 6,753,349 B1
(45) Date of Patent: Jun. 22, 2004

(54) METHOD OF PREPARING VALPROINIC ACID COMPOUNDS

(75) Inventor: Christian Weh, Scheidegg (DE)

(73) Assignee: Cilag AG, Schaffhausen (CH)

( * ) Notice: Subject to any disclaimer, the term of this patent is extended or adjusted under 35 U.S.C. 154(b) by 0 days.

(21) Appl. No.: 10/129,023

(22) PCT Filed: Oct. 31, 2000

(86) PCT No.: PCT/CH00/00578

§ 371 (c)(1),
(2), (4) Date: Jul. 16, 2002

(87) PCT Pub. No.: WO01/32595

PCT Pub. Date: May 10, 2001

(30) Foreign Application Priority Data

Nov. 2, 1999 (CH) .............................................. 1997/99

(51) Int. Cl.$^7$ .......................... A61K 31/19; C07B 53/00
(52) U.S. Cl. ...................... 514/557; 562/606
(58) Field of Search ........................... 514/557; 562/606

(56) References Cited

U.S. PATENT DOCUMENTS

| 4,895,873 | A | 1/1990 | Schäfer | 514/557 |
| 5,017,613 | A | 5/1991 | Aubert et al. | 514/557 |
| 5,795,615 | A | 8/1998 | Nelson et al. | 426/648 |
| 6,077,542 | A | * 6/2000 | Sherman | 424/489 |

FOREIGN PATENT DOCUMENTS

| DE | 0215533 A1 | 11/1984 |
| DE | 215 533 A1 | * 11/1984 |

* cited by examiner

*Primary Examiner*—Richard L. Raymond
*Assistant Examiner*—Zachary C. Tucker
(74) *Attorney, Agent, or Firm*—Hoffmann & Baron, LLP

(57) ABSTRACT

The invention relates to a method for producing compounds which contain at least one molecule valproic acid salt and at least one molecule valproic acid. The valproic acid salt represents alkali or alkaline earth salt. Valproic acid is directly converted with the calculated amount of the corresponding alkali carbonate or earth alkaline carbonate and/or the calculated amount of the corresponding alkali bicarbonate or earth alkaline bicarbonate without adding a solvent and at a temperature that is higher than the melting temperature of valproic acid.

14 Claims, No Drawings

METHOD OF PREPARING VALPROINIC ACID COMPOUNDS

CROSS REFERENCE TO RELATED APPLICATIONS

This application is the National Stage of International Application No. PCT/CH00/00578, filed on Oct. 31, 2000, which claims priority to Swiss Patent Application No. CH 1997/99, filed Nov. 2, 1999, and which are incorporated by reference herein.

FIELD OF THE INVENTION

The present invention relates to a method of preparing oligomeric valproic acid compounds, especially a method of preparing selected oligomeric valproic acid compounds, without the addition of a solvent. Valproic acid is also known as 2-propylpentanoic acid, 2-propylvaleric acid or di-n-propylacetic acid. The term valproic acid is used hereafter.

BACKGROUND OF THE INVENTION

Valproic acid and oligomeric compounds are known per se. Valproic acid, sodium valproate and the oligomeric 1:1 compound of sodium valproate and valproic acid, called divalproex sodium, are active ingredients for the medicinal treatment of epileptic fits, cramp and migraine. Valproic acid is liquid at room temperature and is therefore unsuitable for the preparation of solid pharmaceutical formulations such as tablets. Sodium valproate is solid at room temperature but is very hygroscopic, which makes it very difficult to prepare solid pharmaceutical formulations for oral administration. Divalproex sodium is less hygroscopic, but the compound has a tendency to form lumps and become encrusted on prolonged storage.

SUMMARY OF THE INVENTION

The oligomeric valproic acid compounds described below, with different stoichiometries and solvates, represent possible ways of formulating valproic acid which exhibit said disadvantages to a considerably reduced extent, if at all. It is therefore of interest to be able to prepare such compounds in the simplest possible manner. In particular, it has been found that oligomeric compounds of sodium valproate and valproic acid can be prepared without the addition of a solvent to the reaction mixture, which is ecologically and economically advantageous.

The method according to the invention also has the advantage that lengthy and energy-intensive drying processes can be avoided and environmentally relevant aspects, for example minimization of resources, saving of raw materials and energy or waste reduction, can be taken into account. In particular, the method according to the invention enables the active ingredients to be prepared without drying, under mild conditions and with the avoidance of decomposition processes due to temperature.

At the same time, the method according to the invention offers doctors and patients the opportunity to select their preferred active ingredients from the large number of different, equally potent compounds of valproic acid and valproic acid salts, all of these active ingredients having been prepared by processes identical per se.

One particular advantage of the present invention is that the method according to the invention makes it possible to prepare compounds with selected stoichiometries, i.e., with selected proportions of valproic acid salt and valproic acid, which has hitherto been impossible for these compositions via crystallization from organic solvents. Another advantage of the method according to the invention is that it dispenses with the use of sodium valproate as a hygroscopic sodium source.

DETAILED DESCRIPTION OF THE PREFERRED EMBODIMENTS

The present invention relates in particular to a method of preparing compounds containing at least one molecule of valproic acid salt and at least one molecule of valproic acid, the valproic acid salt being an alkali metal or alkaline earth metal salt, characterized in that valproic acid is reacted directly with the calculated amount of the appropriate alkali metal carbonate or alkaline earth metal carbonate and/or the calculated amount of the appropriate alkali metal bicarbonate or alkaline earth metal bicarbonate, without the addition of a solvent, at a temperature above the melting point of valproic acid.

The reaction temperature is preferably 50° C. to 250° C. and particularly preferably 70° C. to 180° C., the carbon dioxide and water formed in the reaction being removed continuously from the reaction mixture. The valproic acid reacts directly and completely with the carbonate (e.g. $Na_2CO_3$, $CaCO_3$) or the bicarbonate (e.g. $LiHCO_3$, $Ca(HCO_3)_2$) to form $CO_2$ and water. If the compound is to be prepared as a hydrate, the calculated amount of water is added to the product, preferably after the reaction has ended.

An alkali metal salt of valproic acid is preferably the lithium, sodium, potassium or rubidium salt and particularly preferably the sodium or potassium salt. An alkaline earth metal salt of valproic acid is preferably the magnesium, calcium, strontium or barium salt and particularly preferably the magnesium or calcium salt.

The compounds according to the present invention, which contain at least one molecule of valproic acid salt and at least one molecule of valproic acid, have general formula (I):

$$[(CH_3CH_2CH_2)_2CH-C(O)OMe]_m \cdot [(CH_3CH_2CH_2)_2CH-C(O)OH]_n \cdot xH_2O \quad (I)$$

in which

Me is $Li^+$, $Na^+$, $K^+$, $Rb^+$, $Mg^{2+}$, $Ca^{2+}$, $Sr^{2+}$ or $Ba^{2+}$, preferably $Na^+$, $K^+$, 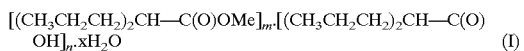 $Mg^{2+}$ or $Ca^{2+}$;

m is an integer from 1 to 10, preferably from 1 to 6, n is an integer from 1 to 9, preferably from 1 to 3, and the ratio m:n is from 1:1 to 6:1, preferably 1:1 to 5:3 and particularly preferably 1:1, 4:3 or 2:1; and x is zero, 1 or 2, preferably zero or 1.

In the Examples which follow, the numbers in brackets indicate the ratio (m+n:m) in each case. Examples of compounds of formula (I) are: 2-propylpentanoic acid (2:1) sodium salt; 2-propylpentanoic acid (2:1) sodium salt monohydrate and dihydrate; 2-propylpentanoic acid (3:2) sodium salt; 2-propylpentanoic acid (4:3) sodium salt; 2-propylpentanoic acid (4:3) sodium salt monohydrate; 2-propylpentanoic acid (5:3) sodium salt; 2-propylpentanoic acid (7:6) sodium salt and the monohydrate and dihydrate; preferably 2-propylpentanoic acid (m+n:m) sodium salt $xH_2O$ in which m+n is an integer from 3 to 10, m is 1 to (m+n−1) in each case and x is zero, one or two; 2-propylpentanoic acid (2:1) lithium salt; 2-propylpentanoic acid (2:1) lithium salt monohydrate and dihydrate; 2-propylpentanoic acid (4:3) lithium salt; 2-propylpentanoic acid (4:3) lithium salt monohydrate; preferably 2-propylpentanoic acid (m+n:m) lithium salt $xH_2O$ in which m+n is an integer from 2 to 10, m is 1 to (m+n−1) in each case and x is zero, one or two; 2-propylpentanoic acid (2:1) potassium salt; 2-propylpentanoic acid (2:1) potassium salt monohydrate; 2-propylpentanoic acid (3:2) potassium salt; 2-propylpentanoic acid (4:3) potassium salt monohydrate; preferably 2-propylpentanoic acid (m+n:m) potassium salt $xH_2O$ in which m+n is an integer from 2 to 10, m is 1 to (m+n−1) in each case and x is zero, one or two; 2-propylpentanoic acid (2:1) rubidium salt;

2-propylpentanoic acid (2:1) rubidium salt monohydrate; 2-propylpentanoic acid (3:2) rubidium salt; 2-propylpentanoic acid (4:3) rubidium salt monohydrate; 2-propylpentanoic acid (m+n:m) rubidium salt $xH_2O$ in which m+n is an integer from 2 to 10, m is 1 to (m+n−1) in each case and x is zero, one or two; preferably 2-propylpentanoic acid (2:1) magnesium salt; 2-propylpentanoic acid (2:1) magnesium salt monohydrate; 2-propylpentanoic acid (3:2) magnesium salt; 2-propylpentanoic acid (4:3) magnesium salt monohydrate; preferably 2-propylpentanoic acid (m+n:m) magnesium salt $xH_2O$ in which m+n is an integer from 3 to 10, m is 1 to (m+n−1) in each case and x is zero, one or two; 2-propylpentanoic acid (2:1) calcium salt; 2-propylpentanoic acid (2:1) calcium salt monohydrate; 2-propylpentanoic acid (3:2) calcium salt; 2-propylpentanoic acid (4:3) calcium salt monohydrate; preferably 2-propylpentanoic acid (m+n:m) calcium salt $xH_2O$ in which m+n is an integer from 3 to 10, m is 1 to (m+n−1) in each case and x is zero, one or two; 2-propylpentanoic acid (2:1) strontium salt; 2-propylpentanoic acid (2:1) strontium salt monohydrate; 2-propylpentanoic acid (3:2) strontium salt; 2-propylpentanoic acid (4:3) strontium salt monohydrate; preferably 2-propylpentanoic acid (m+n:m) strontium salt $xH_2O$ in which m+n is an integer from 2 to 10, m is 1 to (m+n−1) in each case and x is zero, one or two; 2-propylpentanoic acid (2:1) barium salt; 2-propylpentanoic acid (2:1) barium salt monohydrate; 2-propylpentanoic acid (3:2) barium salt; 2-propylpentanoic acid (4:3) barium salt monohydrate; preferably 2-propylpentanoic acid (m+n:m) barium salt $xH_2O$ in which m+n is an integer from 2 to 10, m is 1 to (m+n−1) in each case and x is zero, one or two.

The Examples which follow illustrate the invention.

EXAMPLE 1

144.21 g (1 mol) of liquid valproic acid and an alkali metal carbonate or alkaline earth metal carbonate in the amounts indicated in Table 1 are placed in a round-bottom flask equipped with a stirrer, a reflux condenser and a heater. The mixture is stirred and heated slowly to a temperature above 100° C. (>100° C.), the reaction starting with the formation of $CO_2$ and water. The $CO_2$ and water formed are removed continuously, the $CO_2$ escaping in gaseous form and the water formed being distilled over a descending column. When the reaction has ended, a clear product is obtained which is recovered via a melting plate. The water content of the resulting product is determined by the Karl-Fischer method and the water deficiency is made up if a particular hydrate is to be prepared.

TABLE 1

| Exp. no. | Valproic acid (gram, mol) | Carbonate/ bicarbonate used (gram, gram equivalent) | Water (gram, gram, equivalent) | (m + n):m |
|---|---|---|---|---|
| 1 | 144.21 g, 1.0 mol | $Na_2CO_3$ (35.33 g, 0.33 mol) | 0 | 3:2 |
| 2 | 144.21 g, 1.0 mol | $Na_2CO_3$ (31.80 g, 0.30 mol) | 0 | 5:3 |
| 3 | 144.21 g, 1.0 mol | $Na_2CO_3$ (39.75 g, 0.38 mol) | (4.50 g, 0.25 mol) | 4:3 |
| 4 | 144.21 g, 1.0 mol | $K_2CO_3$ (34.55 g, 0.25 mol) | 0 | 2:1 |
| 5 | 144.21 g, 1.0 mol | $Rb_2CO_3$ (57.74 g, 0.25 mol) | 0 | 2:1 |
| 6 | 144.21 g, 1.0 mol | $NaHCO_3$ (42.01 g, 0.50 mol) | 0 | 2:1 |

TABLE 1-continued

The samples were subjected to elemental analysis. Also, phase analysis was carried out by means of X-ray diffraction (XRD) on powder preparations. Examples of such analyses are as follows:

| 2-Propylpentanoic acid (4:3) sodium salt monohydrate (OMNIVAL I) | | |
|---|---|---|
| triclinic unit cell: | figure of merit M = 12.6 | |
| $a_o$ = 15.9 | $b_o$ = 13.5 | $c_o$ = 5.4 |
| alpha = 101° | beta = 97° | gamma = 111° |
| cell volume 1025 | | |
| 5 molecules in the unit cell give an X-ray density of 1.27 g/cm³. | | |

| 2-Propylpentanoic acid (3:2) sodium salt (OMNIVAL II) | | |
|---|---|---|
| triclinic unit cell: | figure of merit M = 5.4 | |
| $a_o$ = 15.5 | $b_o$ = 13.0 | $c_o$ = 10.4 |
| alpha = 89° | beta = 93° | gamma = 110° |
| cell volume 1973 | | |
| 9 molecules in the unit cell give an X-ray density of 1.20 g/cm³. | | |

What is claimed is:

1. Method of preparing compounds containing at least one molecule of valproic acid salt and at least one molecule of valproic acid, comprising:

selecting an amount of alkali metal carbonate, alkaline earth metal carbonate, alkali metal bicarbonate, alkaline earth metal bicarbonate, or combinations thereof;

selecting an amount of valproic acid;

combining the valproic acid directly with the selected amount of alkali metal carbonate, alkaline earth metal carbonate, alkali metal bicarbonate, alkaline earth metal bicarbonate, or combinations thereof to form a reaction mixture;

reacting valproic acid directly with the selected amount of alkali metal carbonate, alkaline earth metal carbonate, alkali metal bicarbonate, alkaline earth metal bicarbonate, or combinations thereof in the absence of a solvent; and controlling a reaction temperature above the melting point of the valproic acid;

wherein the valproic acid salt is an alkali metal or alkaline earth metal salt.

2. Method according to claim 1, wherein the reaction temperature is from about 50° C. to about 250° C.

3. Method according to claim 1, wherein the reaction temperature is from about 70° C. to 180° C.

4. Method according to claim 1, further comprising the step of continuously removing carbon dioxide and water, which are formed during the step of reacting the valproic acid directly with the selected amount of alkali metal carbonate, alkaline earth metal carbonate, alkali metal bicarbonate, alkaline earth metal bicarbonate, or combinations thereof in the absence of a solvent, from the reaction mixture.

5. Method according to claim 1, further comprising the step of adding an amount of water to the reaction mixture to form a hydrate after the step of reacting the valproic acid directly with the selected amount of alkali metal carbonate, alkaline earth metal carbonate, alkali metal bicarbonate, alkaline earth metal bicarbonate, or combinations thereof in the absence of a solvent.

6. Method according to claim 1, wherein the alkali metal salt of valproic acid is a lithium, a sodium, a potassium or a rubidium salt.

7. Method according to claim 1, wherein the alkali metal salt of valproic acid is a sodium or a potassium salt.

8. Method according to claim 1, wherein the alkaline earth metal salt of valproic acid is a magnesium, calcium, strontium or barium salt.

9. Method according to claim 1, wherein the alkaline earth metal salt of valproic acid is a magnesium or a calcium salt.

10. Method according to claim 1, wherein a compound of general formula (I):

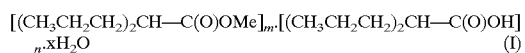

$[(CH_3CH_2CH_2)_2CH-C(O)OMe]_m \cdot [(CH_3CH_2CH_2)_2CH-C(O)OH]_n \cdot xH_2O$ (I)

is prepared in which
Me is $Li^+$, $Na^+$, $K^+$, $Rb^+$, $Mg^{2+}$, $Ca^{2+}$, $Sr^{2+}$ or $Ba^{2+}$;
m is an integer from 1 to 10,
n is an integer from 1 to 9,
and the ratio m:n is from 1:1 to 6:1; and
x is zero, 1 or 2.

11. Method according to claim 10, wherein
Me is $Na^+$, $K^+$, $Mg^{2+}$ or $Ca^{2+}$;
m is an integer from 1 to 6,
n is an integer from 1 to 3,
and the ratio m:n is from 1:1 to 5:3; and
x is zero or 1.

12. Method according to claim 10, wherein the ratio m:n is about 1:1, about 4:3 or about 2:1.

13. Method according to claim 1, wherein a compound of 2-propylpentanoic acid (3:2) sodium salt of the formula

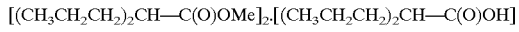

$[(CH_3CH_2CH_2)_2CH-C(O)OMe]_2 \cdot [(CH_3CH_2CH_2)_2CH-C(O)OH]$ is prepared.

14. Method according to claim 1, wherein a compound of 2-propylpentanoic acid (4:3) sodium salt monohydrate of the formula

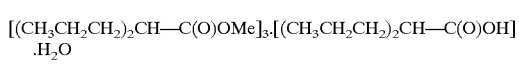

$[(CH_3CH_2CH_2)_2CH-C(O)OMe]_3 \cdot [(CH_3CH_2CH_2)_2CH-C(O)OH] \cdot H_2O$ is prepared.

* * * * *